US012617744B2

(12) United States Patent
Tanizaki et al.

(10) Patent No.: US 12,617,744 B2
(45) Date of Patent: May 5, 2026

(54) PRODUCTION METHOD FOR REDUCED COENZYME Q10 FORM-II TYPE CRYSTAL OR CRYSTALLINE SOLID THEREOF

(71) Applicant: KANEKA CORPORATION, Osaka (JP)

(72) Inventors: Subaru Tanizaki, Takasago (JP); Tadao Ono, Takasago (JP); Takanori Hashimoto, Takasago (JP)

(73) Assignee: KANEKA CORPORATION, Osaka (JP)

( * ) Notice: Subject to any disclaimer, the term of this patent is extended or adjusted under 35 U.S.C. 154(b) by 483 days.

(21) Appl. No.: 18/281,592

(22) PCT Filed: Mar. 4, 2022

(86) PCT No.: PCT/JP2022/009361
§ 371 (c)(1),
(2) Date: Sep. 12, 2023

(87) PCT Pub. No.: WO2022/202214
PCT Pub. Date: Sep. 29, 2022

(65) Prior Publication Data
US 2024/0158330 A1      May 16, 2024

(30) Foreign Application Priority Data
Mar. 26, 2021    (JP) ................................. 2021-052652

(51) Int. Cl.
C07C 46/10          (2006.01)
C07C 50/28          (2006.01)

(52) U.S. Cl.
CPC .......... C07C 46/10 (2013.01); C07B 2200/13 (2013.01)

(58) Field of Classification Search
CPC ...... C07C 46/10; C07C 50/28; C07B 2200/13
See application file for complete search history.

(56) References Cited

U.S. PATENT DOCUMENTS

| | | | |
|---|---|---|---|
| 6,184,255 B1 | 2/2001 | Mae et al. | |
| 8,853,464 B2 * | 10/2014 | Ueda ...................... | C07C 41/40 |
| | | | 568/651 |
| 9,440,901 B2 * | 9/2016 | Kawachi ................. | C07C 41/40 |
| 9,532,957 B2 * | 1/2017 | Ueda ...................... | A61K 47/14 |
| 2004/0214301 A1 | 10/2004 | Ueda et al. | |
| 2014/0120073 A1 | 5/2014 | Kawachi et al. | |
| 2021/0317057 A1 | 10/2021 | Yamaguchi et al. | |

FOREIGN PATENT DOCUMENTS

| | | | |
|---|---|---|---|
| JP | 10-109933 A | 4/1998 | |
| JP | 2003-89669 A | 3/2003 | |
| WO | WO 03/006409 A1 | 1/2003 | |
| WO | WO 2012/176842 A1 | 12/2012 | |
| WO | WO 2020/045571 A1 | 3/2020 | |

OTHER PUBLICATIONS

International Search Report (PCT/ISA/210), issued in PCT/JP2022/009361, dated Apr. 19, 2022.
Written Opinion of the International Searching Authority (PCT/ISA/237), issued in PCT/JP2022/009361, dated Apr. 19, 2022.

* cited by examiner

*Primary Examiner* — Sikarl A Witherspoon
(74) *Attorney, Agent, or Firm* — Birch, Stewart, Kolasch & Birch, LLP

(57) ABSTRACT

It is an object of the present disclosure to provide a method for producing a reduced coenzyme Q10 Form II crystal or a crystalline solid thereof, which is excellent in the filterability of a slurry containing a reduced coenzyme Q10 Form II crystal.
The present embodiment is a method for producing a reduced coenzyme Q10 Form II crystal or a crystalline solid thereof, including: adding a reduced coenzyme Q10 Form II crystal as a seed crystal to a mixed solution containing an alcohol and a reduced coenzyme Q10; and precipitating a reduced coenzyme Q10 Form II crystal in the mixed solution after adding the seed crystal, wherein a change rate of formazin turbidity (FTU) is maintained at 15 FTU/min or more for 80% or more of a period during which the formazin turbidity (FTU) shifts from 1,000 to 10,000 in the precipitation.

8 Claims, No Drawings

PRODUCTION METHOD FOR REDUCED COENZYME Q10 FORM-II TYPE CRYSTAL OR CRYSTALLINE SOLID THEREOF

TECHNICAL FIELD

The present disclosure relates to a method for producing a reduced coenzyme Q10 Form II crystal or a crystalline solid thereof.

BACKGROUND ART

Coenzyme Q is an essential component widely distributed in living organisms from bacteria to mammals, and is known as a member of mitochondrial electron transfer system in cells in the living organisms. Coenzyme Q engages in electron transfer in the electron transfer system by the repetition of oxidation and reduction in mitochondria. Further, reduced coenzyme Q is known to have antioxidant activity. The major component in humans is coenzyme Q10 which is one having 10 repeating structures in the side chain of coenzyme Q, and usually, about 40% to 90% thereof is present in the living body as the reduced form. The physiological activity of coenzyme Q includes activation of energy production by mitochondrial activation, activation of cardiac function, an effect of stabilizing cell membranes, and an effect of protecting cells by antioxidant activity.

While coenzyme Q10 currently produced and sold is, in large part, oxidized coenzyme Q10, reduced coenzyme Q10 which exhibits higher oral absorbability than that of oxidized coenzyme Q10 has also been commercially available and has come to be used in recent years.

A common method for obtaining reduced coenzyme Q10 has already been disclosed (Patent Literature 1). Furthermore, several methods for obtaining reduced coenzyme Q10 as a crystal have also been known. For example, a method of crystallizing reduced coenzyme Q10 in an alcohol solution and/or a ketone solution to produce a crystal (Patent Literature 2), a method of adding a high concentration liquid phase of reduced coenzyme Q10 into a poor solvent for crystallization (Patent Literature 3), and the like have been reported.

On the other hand, Patent Literature 4 reports that crystal polymorphism is found in reduced coenzyme Q10. It has been reported that a newly appearing crystal form (wherein this crystal is hereinafter referred to as a "reduced coenzyme Q10 Form II crystal or Form II crystal") is much more stable than the conventional reduced coenzyme Q10 (wherein this crystal is hereinafter referred to as a "reduced coenzyme Q10 Form I crystal or Form I crystal") and also, is excellent in other physical properties. In addition, Patent Literature 5 reports a method for producing a reduced coenzyme Q10 Form II crystal. Patent Literature 5 discloses a method for producing a reduced coenzyme Q10 Form II crystal, which comprises: adding a reduced coenzyme Q10 Form II crystal as a seed crystal to a solution with a temperature of 32° C. to 43° C., containing at least one organic solvent selected from the group consisting of an alcohol, a hydrocarbon, an aliphatic acid ester and a nitrogen compound, and reduced coenzyme Q10, to prepare a mixed solution; and precipitating a reduced coenzyme Q10 Form II crystal in the mixed solution, in claim 1.

CITATION LIST

Patent Literature

Patent Literature 1: JP Patent Publication No. H10-109933 A

Patent Literature 2: WO2003/006409
Patent Literature 3: JP Patent Publication No. 2003-089669 A
Patent Literature 4: WO2012/176842
Patent Literature 5: WO2020/045571

SUMMARY OF INVENTION

Technical Problem

Patent Literature 4 discloses a method for obtaining a reduced coenzyme Q10 Form II crystal, in which crystallization is carried out under specific conditions. However, there is a case where it takes a long period of time and the recovered amount is small. Thus, it cannot be necessarily said that this method is industrially optimal. The method disclosed in Patent Literature 5 is intended to provide an efficient production method for obtaining a reduced coenzyme Q10 Form II crystal, wherein the production method is also suitable for production in an industrial scale, which focuses mainly on temperatures.

A reduced coenzyme Q10 Form II crystal is conventionally obtained by solid-liquid separation by means of filtration or the like after obtaining a slurry containing the reduced coenzyme Q10 Form II crystal, followed by appropriate drying or other steps. The present inventors thought that when filtering a slurry containing a reduced coenzyme Q10 Form II crystal, filter cleaning and filter replacement will be necessary with high frequency in the case of poor filterability of the slurry.

The present inventors made studies on a method for producing a reduced coenzyme Q10 Form II crystal with a focus on factors other than temperatures and accordingly found that a slurry containing a reduced coenzyme Q10 Form II crystal obtained by a specific production method is excellent in filterability. Accordingly, it is an object of the present disclosure to provide a method for producing a reduced coenzyme Q10 Form II crystal or a crystalline solid thereof, which is excellent in the filterability of a slurry containing a reduced coenzyme Q10 Form II crystal.

Solution to Problem

When precipitating a reduced coenzyme Q10 Form II crystal in a mixed solution containing alcohol and reduced coenzyme Q10, as the precipitation proceeds, the amount of the reduced coenzyme Q10 Form II crystal in a mixed solution increases, resulting in increased turbidity. The present inventors found that a slurry containing a reduced coenzyme Q10 Form II crystal is made excellent in filterability by controlling the change rate of the turbidity.

Example aspects of the present embodiment are described as follows.

(1) A method for producing a reduced coenzyme Q10 Form II crystal or a crystalline solid thereof, comprising:

adding a reduced coenzyme Q10 Form II crystal as a seed crystal to a mixed solution containing an alcohol and a reduced coenzyme Q10; and precipitating a reduced coenzyme Q10 Form II crystal in the mixed solution after adding the seed crystal, wherein a change rate of formazin turbidity (FTU) is maintained at 15 FTU/min or more for 80% or more of a period during which the formazin turbidity (FTU) shifts from 1,000 to 10,000 in the precipitation.

(2) The method according to (1), wherein the reduced coenzyme Q10 Form II crystal produced has a median diameter (D50) of 80 μm or more.

(3) The method according to (1) or (2), wherein the change rate of formazin turbidity (FTU) is maintained at 110 FTU/min or less for 80% or more of a period during which the formazin turbidity (FTU) shifts from 1,000 to 10,000 in the precipitation.

(4) The method according to any one of (1) to (3), wherein the reduced coenzyme Q10 Form II crystal produced has a median diameter (D50) of 130 μm or less.

(5) The method according to any one of (1) to (4), wherein the alcohol is a monohydric alcohol having 1 to 5 carbon atoms.

(6) The method according to (5), wherein the monohydric alcohol having 1 to 5 carbon atoms is ethanol.

(7) The method according to any one of (1) to (6), wherein the alcohol is an alcohol of 95% or more by weight based on a total amount of water and alcohol.

The present description encompasses the specification in JP Patent Application No. 2021-052652 which serves as the basis of the priority of the present application.

Advantageous Effects of Invention

The method of the present disclosure is excellent in filterability of slurry containing a reduced coenzyme Q10 Form II crystal.

DESCRIPTION OF EMBODIMENTS

Hereinafter, the present invention will be described in detail.

<Reduced Coenzyme Q10>

The "reduced coenzyme Q10" herein may partially include oxidized coenzyme Q10, if it includes reduced coenzyme Q10 as a main component. The "main component" herein means that it is included in a proportion of, for example, 50% by weight or more, usually 60% by weight or more, preferably 70% by weight or more, more preferably 80% by weight or more, further preferably 90% by weight or more, particularly preferably 95% by weight or more, and further particularly preferably 98% by weight or more. Herein, the above-described percentage is the percentage of the reduced coenzyme Q10 to the total weight of coenzyme Q10.

Besides, as mentioned above, the reduced coenzyme Q10 includes two forms of crystal polymorphisms, namely, the conventionally known Form I and a recently newly found Form II. Specifically, the crystal form of reduced coenzyme Q10 having a melting point around 48° C. and showing characteristic peaks at diffraction angles (2θ±0.2°) of 3.1°, 18.7°, 19.0°, 20.2° and 23.0° in powder X-ray (Cu—Kα) analysis is Form I, whereas the crystal form of reduced coenzyme Q10 having a melting point around 52° C. and showing characteristic peaks at diffraction angles (2θ±0.2°) of 11.5°, 18.2°, 19.3°, 22.3°, 23.0° and 33.3° in powder X-ray (Cu—Kα) analysis is Form II. In the present description, the crystal of reduced coenzyme Q10 that satisfies at least one of the following conditions is referred to as a "reduced coenzyme Q10 Form II crystal": when the temperature is increased at a rate of 5° C./min by differential scanning calorimetry (DSC), the reduced coenzyme Q10 crystal has an endothermic peak at 54±2° C.; when the same measurement is carried out at a temperature rising rate of 1° C./min, the reduced coenzyme Q10 crystal has an endothermic peak at 52±2° C.; and in powder X-ray (Cu—Kα) analysis, the reduced coenzyme Q10 crystal shows characteristic peaks at diffraction angles (2θ±0.2°) of 11.5°, 18.2°, 19.3°, 22.3°, 23.0° and 33.3°. Of course, the reduced coenzyme Q10 crystal may satisfy all of said three conditions.

Moreover, the term "crystalline solid" is used in the present description to mean a solid containing therein a portion having a crystal structure and an amorphous portion having no crystal structure. In other words, the "crystalline solid thereof" in the expression "reduced coenzyme Q10 Form II crystal or a crystalline solid thereof" means a "solid containing therein a portion having a crystalline structure of reduced coenzyme Q10 Form II crystal and an amorphous component having no crystalline structure."

<Alcohol>

The present inventors found that the saturation concentration of a Form II crystal is lower than the saturation concentration of a Form I crystal in an alcohol, which makes it possible to efficiently precipitate a reduced coenzyme Q10 Form II crystal using an alcohol as a solvent for reduced coenzyme Q10.

The alcohol is preferably a monohydric alcohol having 1 to 5 carbon atoms. Examples of a monohydric alcohol having 1 to 5 carbon atoms include methanol, ethanol, n-propanol, isopropanol, n-butanol, isobutanol, and n-pentanol. As the alcohol, ethanol is particularly preferable because the saturation concentration of Form II crystal is sufficiently lower than the saturation concentration of Form I crystal and is easy to handle. As the alcohol, those exemplified above may be used alone, or two or more thereof may be mixed and used.

The alcohol used in the present description may be a solvent containing alcohol as a main component, and may be a hydrous alcohol containing water. As for the alcohol, the lower the water content, the easier the selective precipitation of Form II crystals. Therefore, the alcohol concentration with respect to the total amount of water and alcohol is, for example, 80% by weight or more, usually 90% by weight or more, preferably 95% by weight or more, more preferably 97% by weight or more, further preferably 99% by weight or more, and particularly preferably 99.5% by weight or more. An alcohol having an alcohol concentration of 99.5% by weight or more means anhydrous alcohol. In addition, the upper limit of the alcohol concentration is 100% by weight or less.

Particularly preferable alcohols are hydrous ethanol and anhydrous ethanol. The ethanol concentration with respect to the total amount of water and ethanol is, for example, 80% by weight or more, usually 90% by weight or more, preferably 95% by weight or more, more preferably 97% by weight or more, further preferably 99% by weight or more, and particularly preferably 99.5% by weight or more. In addition, the upper limit of the ethanol concentration is 100% by weight or less.

<Method for Producing Reduced Coenzyme Q10 Form II Crystal or Crystalline Solid Thereof>

The method for producing reduced coenzyme Q10 Form II crystal or a crystalline solid thereof according to the present embodiment comprises: adding a reduced coenzyme Q10 Form II crystal as a seed crystal to a mixed solution containing an alcohol and a reduced coenzyme Q10; and precipitating a reduced coenzyme Q10 Form II crystal in the mixed solution after adding the seed crystal, wherein a change rate of formazin turbidity (FTU) is maintained at 15 FTU/min or more for 80% or more of a period during which the formazin turbidity (FTU) shifts from 1,000 to 10,000 in the precipitation.

The step of adding a reduced coenzyme Q10 Form II crystal as a seed crystal may be referred to as "seed crystal addition step" and the step of precipitating a reduced coenzyme Q10 Form II crystal may be referred to as "crystal precipitation step" in the following description.

A mixed solution containing alcohol and reduced coenzyme Q10 is not particularly limited as long as it contains alcohol and reduced coenzyme Q10. It may be a solution in which reduced coenzyme Q10 is homogeneously dissolved in alcohol or a slurry in which reduced coenzyme Q10 is partially dissolved but partially not dissolved and suspended in alcohol. Preferably, it is a solution in which reduced coenzyme Q10 is homogeneously dissolved in alcohol.

Reduced coenzyme Q10 used in a mixed solution containing alcohol and reduced coenzyme Q10 may be either a crystalline or amorphous state, and the crystal polymorphism thereof is not limited. Accordingly, a conventionally known reduced coenzyme Q10 Form I can also be used. In addition, since the purity of reduced coenzyme Q10 can be increased in crystal precipitation, reduced coenzyme Q10 having impurities, or unpurified or roughly purified reduced coenzyme Q10 may also be used. Furthermore, an extract of reduced coenzyme Q10 obtained by a conventionally known method, or a reaction solution containing reduced coenzyme Q10 obtained from oxidized coenzyme Q10 by a known reduction method may also be used as the mixed solution, directly, or after purification and/or solvent substitution, as necessary.

The mixed solution containing alcohol and reduced coenzyme Q10 may further include an organic solvent other than alcohol (including hydrous alcohol). The content of alcohol (alcohol purity) in the total amount of solvent components is preferably 95% by weight or more, 97% by weight or more, or 99% by weight or more. The upper limit thereof is preferably 100% by weight or less. The alcohol purity is most preferably 99.5% by weight or more. Examples of other organic solvents may include at least one selected from the group consisting of a hydrocarbon, an aliphatic acid ester, and a nitrogen compound.

The concentration of dissolved reduced coenzyme Q10 before seed crystal addition in the mixed solution containing alcohol and reduced coenzyme Q10 is, for example, 2% by weight or more, preferably 3% by weight or more, more preferably 5% by weight or more, further preferably 7% by weight or more, and particularly preferably 9% by weight or more. The concentration of dissolved reduced coenzyme Q10 before seed crystal addition is, for example, 50% by weight or less, preferably 45% by weight or less, more preferably 30% by weight or less, further preferably 20% by weight or less, and particularly preferably 15% by weight or less.

A mixed solution containing alcohol and reduced coenzyme Q10 can be obtained by heating a raw material mixture containing alcohol and reduced coenzyme Q10 to a temperature of, for example, 42° C. or higher to dissolve reduced coenzyme Q10. The temperature is preferably 70° C. or lower, more preferably 55° C. or lower. Before adding a seed crystal after dissolving reduced coenzyme Q10, it is preferable to cool the mixed solution containing alcohol and reduced coenzyme Q10 to a temperature when adding a seed crystal, as described later.

The added amount of the reduced coenzyme Q10 Form II crystal serving as a seed crystal (the added amount of seed crystal) is not particularly limited. The added amount of the reduced coenzyme Q10 Form II crystal serving as a seed crystal is preferably 0.1% by weight or more, more preferably 0.5% by weight or more, further preferably 0.8% by weight or more, and particularly preferably 1% by weight or more, based on the amount of the reduced coenzyme Q10 in the mixed solution before seed crystal addition (100% by weight). The upper limit thereof is not particularly limited, but is preferably 20% by weight or less, more preferably 4% by weight or less, and further preferably 2.2% by weight or less, based on the amount of the reduced coenzyme Q10 in the mixed solution before seed crystal addition (100% by weight). Besides, the reduced coenzyme Q10 crystal used as a seed crystal may also comprise reduced a coenzyme Q10 Form I crystal or an amorphous solid, as long as the reduced coenzyme Q10 crystal comprises a reduced coenzyme Q10 Form II crystal. However, the higher the purity of reduced coenzyme Q10 Form II crystal, the more preferable. Thus, it may be preferable to use, as a seed crystal, a reduced coenzyme Q10 crystal comprising, for example, 50% by weight or more of, preferably 75% by weight or more of, more preferably 80% by weight or more of, and further preferably 90% by weight or more of reduced coenzyme Q10 Form II crystal.

The temperature of the mixed solution when adding a seed crystal is preferably 30° C. to 43° C. The temperature of the mixed solution when adding a seed crystal is more preferably 32° C. or higher, particularly preferably 34° C. or higher, and further preferably 40° C. or less. Selective precipitation of reduced coenzyme Q10 Form II crystal is easy in this range.

The crystal precipitation step comprises maintaining the change rate of formazin turbidity (FTU) at 15 FTU/min or more for 80% or more of a period during which the formazin turbidity (FTU) shifts from 1,000 to 10,000. The change rate of formazin turbidity (FTU) is preferably 16 FTU/min or more, more preferably 18 FTU/min or more, and further preferably 20 FTU/min or more. As the crystal precipitation proceeds, the formazin turbidity (FTU) increases. Filterability of a slurry containing a reduced coenzyme Q10 Form II crystal is made excellent by maintaining the change rate of formazin turbidity (FTU) at 15 FTU/min or more for 80% or more of a period during which the formazin turbidity (FTU) shifts from 1,000 to 10,000. The present inventors presume that this is because an increase in the formazin turbidity (FTU) means that crystal precipitation is progressing, and by setting the change rate of formazin turbidity (FTU) to a specific range, it is possible to suppress the formation of crystals having small median diameters due to moderate precipitation. In addition, even in a case in which the change rate of formazin turbidity (FTU) is outside the specific range in a part of the period during which the formazin turbidity (FTU) shifts from 1,000 to 10,000, a reduced coenzyme Q10 Form II crystal having excellent filterability can be stably produced as long as the change rate of formazin turbidity (FTU) is within the specific range for 80% or more of a period during which the formazin turbidity (FTU) shifts from 1,000 to 10,000. The time equal to 80% or more of a period during which the formazin turbidity (FTU) shifts from 1,000 to 10,000 means, for example, 240 minutes or longer and 720 minutes or longer when the shift from 1,000 to 10,000 (FTU) requires 300 minutes and 900 minutes, respectively.

It is preferable that reduced coenzyme Q10 is homogeneously dissolved in alcohol in the mixed solution when adding a seed crystal. The formazin turbidity (FTU) of the mixed solution when adding a seed crystal is usually 0 to 250, preferably 0 to 230, and more preferably 0 to 200. This range is preferable because reduced coenzyme Q10 Form II crystals are preferentially precipitate.

The change rate of formazin turbidity (FTU) at a certain time point (T) can be calculated by the following formula:

$$\text{Change rate of formazin turbidity}_T \text{ (FTU/min)}=(\text{Turbidity measurement value}_T \text{ (FTU)}-\text{Turbidity measurement value}_{T-20} \text{ (FTU)})/20 \text{ (min)}$$

(in the formula, the change rate of formazin turbidity$_T$ means a change rate of formazin turbidity (FTU) at a time point (T), the turbidity measurement value$_T$ (FTU) means a measurement value of formazin turbidity (FTU) at a time point (T), and the turbidity measurement value$_{T-20}$ (FTU) means a measurement value of formazin turbidity (FTU) 20 minutes before the time point (T)).

In other words, the change rate of formazin turbidity (FTU) can be calculated by measuring the formazin turbidity (FTU) at 20-minute intervals and dividing the increase (FTU) during the measurement by 20 (min) in the present embodiment. In short, even when the change rate of formazin turbidity (FTU) is outside the range of the present embodiment for a very short period (e.g., 1 minute) in one hypothetical embodiment, in a case in which the change rate of formazin turbidity (FTU) is within the range of the change rate of formazin turbidity (FTU) according to the present embodiment during the measurement at 20-minute intervals, the hypothetical embodiment is considered to satisfy the change rate of formazin turbidity (FTU) according to the present embodiment.

The change rate of formazin turbidity (FTU) is maintained at 110 FTU/min or less, more preferably 90 FTU/min or less, and further preferably 60 FTU/min or less for 80% or more of a period during which the formazin turbidity (FTU) shifts from 1,000 to 10,000.

In the present embodiment, it is one preferred aspect that the change rate of formazin turbidity (FTU) is maintained in the above-described specific range, which is, for example, 15 FTU/min or more and preferably 20 FTU/min or more, in the entire period (100%) during which the formazin turbidity (FTU) shifts from 1,000 to 10,000. It is also a preferred aspect that the change rate of formazin turbidity (FTU) is maintained at 110 FTU/min or less, preferably 85 FTU/min or less, and more preferably 60 FTU/min or less in the entire period (100%) during which the formazin turbidity (FTU) shifts from 1,000 to 10,000.

The temperature of the mixed solution in the period during which the formazin turbidity (FTU) shifts from 1,000 to 10,000 is preferably 30° C. to 43° C., more preferably 30.5° C. to 42° C., and particularly preferably 31° C. to 41° C. This range of the temperature of the mixed solution is preferable because it is easy to maintain change rate of formazin turbidity (FTU) within the above-described range.

The temperature of the mixed solution at 10,000 FTU is preferably 29° C. to 38° C., more preferably 30° C. to 37° C., and particularly preferably 31° C. to 36° C.

The temperature of the mixed solution in the crystal precipitation step can be appropriately adjusted depending on the formazin turbidity and the change rate of formazin turbidity (FTU) at the time of crystal precipitation. The temperature of the mixed solution may be constant but may be lowered stepwise or continuously. In addition, the temperature of the mixed solution may be maintained at a constant temperature for a certain period and then lowered stepwise or continuously. In one preferred aspect, the temperature of the mixed solution when adding a seed crystal is 34° C. to 38° C. and the temperature of the mixed solution at 10,000 FTU is 30° C. to 37° C. It is preferable that the temperature at 10,000 FTU is lower by 0.4° C. to 8° C. than the temperature when adding a seed crystal. Maintaining a constant temperature means preferably maintaining a predetermined temperature (set temperature)±3° C. and more preferably maintaining a predetermined temperature (set temperature)±1° C.

The cooling rate for reducing the temperature of the mixed solution is preferably 0.05° C./hr to 20° C./hr and more preferably 0.1° C./hr to 15° C./hr. In a preferred aspect, the cooling rate may be changed over time. For instance, an aspect in which the temperature is maintained for a certain period, e.g., 0.5 to 8 hours after seed crystal addition, following which the cooling rate is set to 0.05° C./hr to less than 0.5° C./hr for 3 to 20 hours, and then 0.5° C./hr to 15° C./hr and an aspect in which after seed crystal addition, the cooling rate is set to 0.05° C./hr to less than 0.5° C./hr for 3 to 20 hours, and then 0.5° C./hr to 15° C./hr can be mentioned.

It is preferable to lower the temperature of the mixed solution also after the formazin turbidity reaches 10,000 FTU for crystal precipitation in the crystal precipitation step. The cooling rate at that time can be set, for example, based on the range described above. When the temperature of the mixed solution reaches 23° C. to 34° C., most of the reduced coenzyme Q10 contained in the mixed solution has been precipitated. Therefore, it is also possible to increase the cooling rate to a range of 1° C./hr to 20° C./hr after the temperature reaches 23° C. to 34° C., for example.

The temperature at which the crystal precipitation step ends, namely the end point temperature, is preferably 25° C. or lower, more preferably 20° C. or lower, still more preferably 10° C. or lower, yet still more preferably 7° C. or lower, and even still more preferably 5° C. or lower. The lower limit of the end point temperature is the solidification temperature of the mixed solution system, which is preferably 0° C. or higher.

Crystal precipitation is preferably carried out while forced-flowing the mixed solution. From the viewpoint of suppressing the formation of supersaturation and smoothly conducting nucleation and/or crystal growth, or from the viewpoint of the achievement of high quality, flowing may be given to the mixed solution at a power required for stirring per unit volume of generally 0.003 kW/m$^3$ or more, preferably 0.004 kW/m$^3$ or more, more preferably 0.005 kW/m$^3$ or more, and further preferably 0.006 kW/m$^3$ or more. In addition, flowing may be given to the mixed solution at a power required for stirring of generally 0.1 kW/m$^3$ or less and preferably 0.03 kW/m$^3$ or less. The forced-flowing is generally given by the rotation of a stirring blade. However, if the above-described flowing is obtained, the use of the stirring blade is not always necessary, and for example, a method involving circulation of the mixed solution or the like may be utilized.

In the crystal precipitation step described above, a mixed solution (slurry) in which a reduced coenzyme Q10 Form II crystal is precipitated can be obtained. The method according to the present embodiment is excellent in filterability of the slurry such that a reduced coenzyme Q10 Form II crystal can be easily recovered from the slurry via filtration.

The reduced coenzyme Q10 Form II crystal obtained by the above method is recovered from slurry through a step of solid-liquid separation and drying by a conventionally known method described in, for example, Patent Literature 2 or 3. For example, pressure filtration or centrifugal filtration can be used for solid-liquid separation. In addition, the crystal or crystalline solid after drying can also be recovered by pulverization or classification (sieving), if necessary.

The median diameter (D50) of the reduced coenzyme Q10 Form II crystal obtained by the above-described method is preferably 80 μm or more, more preferably 83 μm or more, and particularly preferably 85 μm or more. In addition, the median diameter (D50) of the reduced coenzyme Q10 Form II crystal is 130 μm or less, more preferably 125 μm or less, and particularly preferably 120 μm or less. The median diameter (D50) within the above-described range is preferable because the filterability of slurry containing the reduced coenzyme Q10 Form II crystal is excellent.

In the present embodiment, as one of more preferred aspects, after completion of the aforementioned solid-liquid separation, the reduced coenzyme Q10 Form II crystal is dried with warming, so that the content rate of the reduced coenzyme Q10 Form II crystal can be improved. For this purpose, the drying temperature is preferably 46° C. or higher, more preferably 47° C. or higher, and further preferably 49° C. or higher. The upper limit of the drying temperature is generally 52° C. or lower, and preferably 51° C. or lower. When the drying temperature is lower than 46° C., drying progresses, but the content rate of the reduced coenzyme Q10 Form II crystal is hardly improved. On the other hand, when the drying temperature exceeds 52° C., there may be a case where the reduced coenzyme Q10 crystal is melted during the drying.

Besides, when the desired content rate of the reduced coenzyme Q10 Form II crystal has already been achieved in the crystal precipitation step, the aforementioned drying conditions may not apply, and the drying may be carried out at a temperature of, for example, 25° C. or higher, preferably 30° C. or higher, and more preferably 35° C. or higher.

In addition, the warming time in the case of performing drying is not particularly limited, but it is preferably 4 hours or more, more preferably 10 hours or more, and further preferably 20 hours or more. The upper limit of the warming time is not particularly limited, but it is usually 72 hours or less, preferably 48 hours or less, and more preferably 36 hours or less.

Besides, individual steps in the method of the present embodiment, specifically, the above-described seed crystal addition step, crystal precipitation step, recovery step such as solid-liquid separation or drying, and other treatment steps are preferably performed under a deoxygenated atmosphere. The deoxygenated atmosphere can be achieved by the replacement of the atmosphere with an inert gas, reduction of the pressure, boiling, or a combination thereof. The replacement of the atmosphere with an inert gas, namely, an inert gas atmosphere is preferably used. Examples of the inert gas include nitrogen gas, helium gas, argon gas, hydrogen gas, and carbon dioxide, and preferably nitrogen gas.

Whether or not the reduced coenzyme Q10 Form II crystal is contained in the obtained reduced coenzyme Q10 crystal or a crystalline solid thereof, and the content rate thereof can be determined by measuring with, for example, a differential scanning calorimeter (DSC).

As mentioned above, when the reduced coenzyme Q10 Form II crystal is measured with DSC at a temperature rising rate of 1 C/min, it exhibits an endothermic peak around 52±2° C. On the other hand, the reduced coenzyme Q10 Form I crystal exhibits an endothermic peak around 48±1° C. under the same conditions as those described above. Even in a state in which the reduced coenzyme Q10 Form II crystal is mixed with the conventional reduced coenzyme Q10 Form I crystal or a crystalline solid thereof, the presence or absence of the reduced coenzyme Q10 Form II crystal or the content rate thereof can be determined based on the presence or absence of the above-described peak around 52±2° C., the height of the endothermic peak, or the ratio of the endothermic amount. According to the present invention, the slurry containing the reduced coenzyme Q10 Form II crystal is excellent in filterability. According to the method for producing a reduced coenzyme Q10 Form II crystal or a crystalline solid thereof of the present invention, it is possible to reduce the frequency of filter cleaning and filter replacement. Thus, the method is excellent in productivity. According to the present embodiment, a reduced coenzyme Q10 Form II crystal can be obtained by the crystal precipitation step. A crystalline solid may be obtained by partially melting the crystal by the subsequent drying step or the like. Therefore, the present embodiment also encompasses a case in which a crystal is obtained and a case in which a crystalline solid is obtained.

EXAMPLES

Hereinafter, the present embodiment will be described with reference to Examples. However, the present disclosure is not limited by these Examples.

<Method for Evaluating Filterability>

The slurries obtained in Examples and Comparative Example were subjected to constant pressure filtration with a filtrate volume of 200 mL and a filtration pressure of 0.1 hPa and the filtration rate was measured. The average specific filtration resistance ($\alpha_{av}$) was calculated and used for the evaluation of filterability.

<Device for Measuring Median Diameter>

The median diameters of reduced coenzyme Q10 crystals obtained in Examples and Comparative Example were measured using the device described below.

Particle size distribution analyzer: Partica LA-960

<Percentage of Form II Crystal in Reduced Coenzyme Q10 Crystal>

The reduced coenzyme Q10 crystals obtained in Examples and Comparative Example were analyzed by DSC measurement under the following conditions. From the height (Difference Y) of the endothermic peak of the obtained reduced coenzyme Q10 Form I crystal (hereinafter referred to as "Difference Form I-Y") and the height (Difference Y) of the endothermic peak of the obtained reduced coenzyme Q10 Form II crystal obtained (hereinafter referred to as "Difference Form II-Y," the percentage of the reduced coenzyme Q10 Form II crystal in each reduced coenzyme Q10 crystal was calculated based on the following formula:

$$\text{Form } II \text{ percentage (\%)} = \text{Difference Form } II\text{-}Y/(\text{Difference Form } I\text{-}Y + \text{Difference Form } II\text{-}Y) \times 100$$

(DSC Measurement Conditions)

Apparatus: DSC 6220 (manufactured by SII Nano Technology Inc.)

Sample container: Aluminum pan & cover (SSC000C008)

Rate of temperature rise: 1° C./min

Amount of sample: 5±2 mg

<Method for Determining Change Rate of Formazin Turbidity (FTU)>

For the change rate of formazin turbidity (FTU) in Examples and Comparative Example, the formazin turbidity (FTU) of a mixed solution containing ethanol and reduced coenzyme Q10 was measured with a turbidimeter. The change rate of formazin turbidity (FTU) at a certain time point (T) was calculated by the following formula. In addition, the turbidimeter used in the present embodiment was calibrated to give a turbidity (FTU) of 9,999 FTU when a reduced coenzyme Q10 crystal was present in the mixed solution at a concentration of 40000 mg/L:

Change rate of formazin turbidity$_T$ (FTU/min)=(Tur-
bidity measurement value$_T$ (FTU)−Turbidity
measurement value$_{T-20}$ (FTU))/20 (min)

(in the formula, the change rate of formazin turbidity$_T$ means
a change rate of formazin turbidity (FTU) at a time point (T),
the turbidity measurement value$_T$ (FTU) means a measure-
ment value of formazin turbidity (FTU) at a time point (T),
and the turbidity measurement value$_{T-20}$ (FTU) means a
measurement value of formazin turbidity (FTU) 20 minutes
before the time point (T)). Turbidimeter: Backscattered light
turbidity sensor (InPro8200, METTLER TOLEDO)

Measurement range: 0 to 10,000 FTU

Turbidity (FTU) measurement was carried out immedi-
ately after seed crystal addition until the turbidity reached
10,000 FTU as the upper limit for measurement. The change
rate of formazin turbidity (FTU) was calculated in a period
during which the turbidity was 1,000 to 10,000 FTU. As
shown in the above formula, the change rate of formazin
turbidity (FTU) at a certain time point T was obtained by
calculating the increase in the turbidity (FTU) at the time
point T from the turbidity (FTU) at the time point 20 minutes
before (T−20 min) and dividing the increase by 20 (min).

Example 1

The inside of a separable flask with a volume of 3 L was
replaced with nitrogen, and 144 g of reduced coenzyme Q10
and 1296 g of ethanol having a purity of 99.5% by weight
or more were then charged thereto (reduced coenzyme Q10
concentration: 10 wt %). Thereafter, the obtained mixture
was warmed to 50° C. while stirring with a stirring blade
(power required for stirring: 0.03 kw/m$^3$) to obtain a homo-
geneous reduced coenzyme Q10 solution (QH solution)
(1440 g, 1800 mL).

The QH solution at 50° C. was cooled to 35.0° C. while
stirring with a stirring blade (power required for stirring:
0.03 kw/m$^3$). To the QH solution cooled to 35.0° C. (FTU:
199), 2.9 g (2.0 wt %) of a reduced coenzyme Q10 Form II
crystal was added as a seed crystal to initiate the precipita-
tion of reduced coenzyme Q10 crystal (crystallization).
Hereinafter, the QH solution to which a seed crystal was
added is referred to as "mixed solution for crystallization."

After seed crystal addition, the temperature was main-
tained at 35.0° C. for 1 hour and then cooled from 35.0° C.
to 32.0° C. at 0.2° C./hr (primary cooling). Subsequently,
cooling was carried out at 1° C./hr to reach 25° C. and then
at 10° C./hr from 25° C. to 1° C.

The formazin turbidity (FTU) of a mixed solution for
crystallization was measured with a turbidimeter during
crystallization. It was confirmed that the maximum change
rate of formazin turbidity (FTU) is 32.5 FTU/min in the
entire period during which the formazin turbidity (FTU)
shifts from 1,000 to 10,000 and that the change rate of
formazin turbidity (FTU) is maintained at 15.3 to 32.5
FTU/min for 80% or more of a period during which the
formazin turbidity (FTU) shifts from 1,000 to 10,000.

After cooling to 1° C., a portion of the obtained slurry was
sampled and evaluated for filterability (calculating average
specific filtration resistance ($\alpha_{av}$)). The remaining slurry was
subjected to solid-liquid separation by filtration, and the
resulting crystal was dried under reduced pressure at 40° C.
for 24 hours to obtain a reduced coenzyme Q10 Form II
crystal.

The percentage of Form II crystal in the obtained reduced
coenzyme Q10 crystal was 100%, and thus no reduced
coenzyme Q10 Form I crystal was contained therein. In
addition, the median diameter of the reduced coenzyme Q10 crystal was 115.3 μm, and the average specific filtration
resistance ($\alpha_{av}$) thereof was 0.47×10$^{10}$ m/kg.

Example 2

The inside of a four-necked flask with a volume of 500
mL was replaced with nitrogen, and 33 g of reduced coen-
zyme Q10 and 295 g of ethanol having a purity of 99.5% by
weight or more were then charged thereto (reduced coen-
zyme Q10 concentration: 10 wt %). Thereafter, the obtained
mixture was warmed to 50° C. while stirring with a stirring
blade (power required for stirring: 0.007 kw/m$^3$) to obtain a
homogeneous QH solution (328 g, 410 mL).

The QH solution at 50° C. was cooled to 36.8° C. while
stirring with a stirring blade (power required for stirring:
0.007 kw/m$^3$). To the QH solution cooled to 36.8° C., 0.66
g (2.0 wt %) of a reduced coenzyme Q10 Form II crystal was
added as a seed crystal to initiate the precipitation of reduced
coenzyme Q10 crystal (crystallization).

The set temperature was controlled in order to maintain
the change rate of formazin turbidity (FTU) during which
the formazin turbidity (FTU) of the mixed solution for
crystallization after seed crystal addition shifted from 1,000
to 10,000 to a level of around 55.6 FTU/min. Once the
formazin turbidity reached 10,000 FTU, the temperature was
cooled to 25° C. at 1° C./hr and then from 25° C. to 1° C.
at 10° C./hr. It was confirmed that the maximum and
minimum change rates of formazin turbidity (FTU) are
105.2 FTU/min and 30.6 FTU/min, respectively, in the
entire period during which the formazin turbidity (FTU)
shifts from 1,000 to 10,000 and that the change rate of
formazin turbidity (FTU) is maintained at 81.0 FTU/min or
less for 80% or more of a period during which the formazin
turbidity (FTU) shifts from 1,000 to 10,000.

After cooling to 1° C., a portion of the obtained slurry was
sampled and evaluated for filterability (calculating average
specific filtration resistance ($\alpha_{av}$)). The remaining slurry was
subjected to solid-liquid separation by filtration, and the
resulting crystal was dried under reduced pressure at 40° C.
for 24 hours to obtain a reduced coenzyme Q10 Form II
crystal.

The percentage of Form II crystal in the obtained reduced
coenzyme Q10 crystal was 100%, and thus no reduced
coenzyme Q10 Form I crystal was contained therein. In
addition, the median diameter of the reduced coenzyme Q10
crystal was 87.6 μm, and the average specific filtration
resistance ($\alpha_{av}$) thereof was 0.98×10$^{10}$ m/kg.

Example 3

The inside of a four-necked flask with a volume of 500
mL was replaced with nitrogen, and 33 g of reduced coen-
zyme Q10 and 295 g of ethanol having a purity of 99.5% by
weight or more were then charged thereto (reduced coen-
zyme Q10 concentration: 10 wt %). Thereafter, the obtained
mixture was warmed to 50° C. while stirring with a stirring
blade (power required for stirring: 0.007 kw/m$^3$) to obtain a
homogeneous QH solution (328 g, 410 mL).

The QH solution at 50° C. was cooled to 34.5° C. while
stirring with a stirring blade (power required for stirring:
0.007 kw/m$^3$). To the QH solution cooled to 34.5° C., 0.66
g (2.0 wt %) of a reduced coenzyme Q10 Form II crystal was
added as a seed crystal to initiate the precipitation of reduced
coenzyme Q10 crystal (crystallization).

The set temperature was controlled in order to maintain
the change rate of formazin turbidity (FTU) during which
the formazin turbidity (FTU) of the mixed solution for crystallization after seed crystal addition shifted from 1,000 to 10,000 to a level of around 33.3 FTU/min. Once the formazin turbidity reached 10,000 FTU, the temperature was cooled to 25° C. at 1° C./hr and then from 25° C. to 1° C. at 10° C./hr. It was confirmed that the maximum and minimum change rates of formazin turbidity (FTU) are 41.7 FTU/min and 14.4 FTU/min, respectively, in the entire period during which the formazin turbidity (FTU) shifts from 1,000 to 10,000 and that the change rate of formazin turbidity (FTU) is maintained at 22.5 to 41.7 FTU/min for 80% or more of a period during which the formazin turbidity (FTU) shifts from 1,000 to 10,000.

After cooling to 1° C., a portion of the obtained slurry was sampled and evaluated for filterability (calculating average specific filtration resistance ($\alpha_{av}$)). The remaining slurry was subjected to solid-liquid separation by filtration, and the resulting crystal was dried under reduced pressure at 40° C. for 24 hours to obtain a reduced coenzyme Q10 Form II crystal.

The percentage of form II crystal in the obtained reduced coenzyme Q10 crystal was 100%. In addition, the median diameter of the reduced coenzyme Q10 crystal was 107.3 μm, and the average specific filtration resistance ($\alpha_{av}$) thereof was $0.48 \times 10^{10}$ m/kg.

Comparative Example 1

The inside of a four-necked flask with a volume of 500 mL was replaced with nitrogen, and 28 g of reduced coenzyme Q10 and 250 g of ethanol having a purity of 99.5% by weight or more were then charged thereto (reduced coenzyme Q10 concentration: 10 wt %). Thereafter, the obtained mixture was warmed to 50° C. while stirring with a stirring blade (power required for stirring: 0.007 kw/m³) to obtain a homogeneous QH solution (278 g, 347 mL).

The QH solution at 50° C. was cooled to 36.8° C. while stirring with a stirring blade (power required for stirring: 0.007 kw/m³). To the QH solution cooled to 36.8° C., 0.6 g (2.0 wt %) of a reduced coenzyme Q10 Form II crystal was added as a seed crystal to initiate the precipitation of reduced coenzyme Q10 crystal (crystallization).

The set temperature was controlled in order to maintain the change rate of formazin turbidity (FTU) during which the formazin turbidity (FTU) of the mixed solution for crystallization after seed crystal addition shifted from 1,000 to 10,000 to a level of around 6.9 FTU/min. Once the formazin turbidity reached 10,000 FTU, the temperature was cooled to 25° C. at 1° C./hr and then from 25° C. to 1° C. at 10° C./hr. It was confirmed that the change rate of formazin turbidity (FTU) is maintained at less than 15 FTU/min for 95% or more of a period during which the formazin turbidity (FTU) shifts from 1,000 to 10,000.

After cooling to 1° C., a portion of the obtained slurry was sampled and evaluated for filterability (calculating average specific filtration resistance ($\alpha_{av}$)). The remaining slurry was subjected to solid-liquid separation by filtration, and the resulting crystal was dried under reduced pressure at 40° C. for 24 hours to obtain a reduced coenzyme Q10 Form II crystal.

The percentage of Form II crystal in the obtained reduced coenzyme Q10 crystal was 100%, and thus no reduced coenzyme Q10 Form I crystal was contained therein. In addition, the median diameter of the reduced coenzyme Q10 crystal was 68.2 μm, and the average specific filtration resistance ($\alpha_{av}$) thereof was $3.4 \times 10^{10}$ m/kg.

Table 1 shows the results of Examples and Comparative Example.

TABLE 1

| | $\alpha_{av}$ (m/kg) | Median diameter (μm) | Temperature at 10,000 FTU (° C.) |
|---|---|---|---|
| Example 1 | $0.47 \times 10^{10}$ | 115.3 | 33.8 |
| Example 2 | $0.98 \times 10^{10}$ | 87.6 | 32.8 |
| Example 3 | $0.48 \times 10^{10}$ | 107.3 | 33.1 |
| Comparative Example 1 | $3.4 \times 10^{10}$ | 68.2 | 36.3 |

The slurries obtained in Examples (slurries cooled to 1° C.) had obviously lower average specific filtration resistance ($\alpha_{av}$) and excellent filterability than the slurries obtained in Comparative Example. This shows that when precipitating a reduced coenzyme Q10 Form II crystal in the mixed solution for crystallization after seed crystal addition, the filterability of a slurry containing the reduced coenzyme Q10 Form II crystal is made excellent by maintaining the change rate of formazin turbidity (FTU) for 80% or more of a period during which the formazin turbidity (FTU) shifts from 1,000 to 10,000 in a specific range. In other words, it is understood that by maintaining the change rate of formazin turbidity (FTU) in a specific range, it becomes possible to efficiently recover a reduced coenzyme Q10 Form II crystal by simple filtration, which is excellent in productivity of a reduced coenzyme Q10 Form II crystal or a crystalline solid thereof.

All publications, patents, and patent applications cited in the present description are incorporated herein by reference in their entirety.

The upper and/or lower limits of the numerical ranges described herein can be combined arbitrarily to define a preferred range. For example, a preferred range can be defined by arbitrarily combining the upper and lower limits of the numerical range, a preferred range can be defined by arbitrarily combining the upper limits of the numerical range, and a preferred range can be defined by arbitrarily combining the lower limits of the numerical range.

It should be understood that throughout the present description, expressions in the singular forms also include the concept of their plural forms unless otherwise specifically stated. Thus, articles in the singular forms (e.g., "a," "an," and "the" in the English language) should be understood to include the concept of their plural forms as well, unless otherwise specifically stated.

Although the embodiment of the present invention has been described in detail above, the specific configuration is not limited to this embodiment, and even when there are design changes within the scope of the present disclosure, they are included in the present disclosure.

The invention claimed is:
1. A method for producing a reduced coenzyme Q10 Form II crystal or a crystalline solid thereof, comprising:
   adding a reduced coenzyme Q10 Form II crystal as a seed crystal to a mixed solution containing an alcohol and a reduced coenzyme Q10; and
   precipitating a reduced coenzyme Q10 Form II crystal in the mixed solution after adding the seed crystal,
   wherein a change rate of formazin turbidity (FTU) is maintained at 15 FTU/min or more for 80% or more of a period during which the formazin turbidity (FTU) shifts from 1,000 to 10,000 in the precipitation.
2. The method according to claim 1, wherein the reduced coenzyme Q10 Form II crystal produced has a median diameter (D50) of 80 μm or more.
3. The method according to claim 1, wherein the change rate of formazin turbidity (FTU) is maintained at 110

FTU/min or less for 80% or more of a period during which the formazin turbidity (FTU) shifts from 1,000 to 10,000 in the precipitation.

4. The method according to claim 1, wherein the reduced coenzyme Q10 Form II crystal produced has a median diameter (D50) of 130 μm or less.

5. The method according to claim 1, wherein the alcohol is a monohydric alcohol having 1 to 5 carbon atoms.

6. The method according to claim 5, wherein the monohydric alcohol having 1 to 5 carbon atoms is ethanol.

7. The method according to claim 1, wherein the alcohol is an alcohol of 95% or more by weight based on a total amount of water and alcohol.

8. The method according to claim 2, wherein the reduced coenzyme Q10 Form II crystal produced has a median diameter (D50) of 130 μm or less.

\* \* \* \* \*